United States Patent [19]

Navon et al.

[11] Patent Number: 5,479,924
[45] Date of Patent: Jan. 2, 1996

[54] METHOD OF MEASURING THE $^{17}$O CONTENT AND DISTRIBUTION IN A BODY

[75] Inventors: Gil Navon, Ramat Gan; Itamar Ronen, Tel Aviv, both of Israel

[73] Assignee: British Technology Group Ltd., London, England

[21] Appl. No.: 259,865

[22] Filed: Jun. 15, 1994

[30] Foreign Application Priority Data

Jun. 18, 1993 [IE] Ireland .................................... 106066

[51] Int. Cl.$^6$ .................................................. A61B 5/055
[52] U.S. Cl. .................................. 128/653.2; 128/653.4; 128/654
[58] Field of Search ........................ 128/653.2, 653.3, 128/653.4, 654; 324/309

[56] References Cited

U.S. PATENT DOCUMENTS

| | | | |
|---|---|---|---|
| 3,764,892 | 10/1973 | Rollwitz | 324/309 |
| 4,442,404 | 4/1984 | Bergmann | 324/309 |
| 4,769,604 | 9/1988 | Sepponen | 324/309 |
| 4,996,041 | 2/1991 | Arai et al. | 128/653.4 |
| 5,339,814 | 8/1994 | Lasker | 128/653.4 |

FOREIGN PATENT DOCUMENTS

| | | |
|---|---|---|
| 118281A3 | 9/1984 | European Pat. Off. . |
| 455836A1 | 11/1991 | European Pat. Off. . |
| 90/01953 | 3/1990 | WIPO . |

OTHER PUBLICATIONS

T. Arai et al., "In Vivo Oxygen–17 Nuclear Magnetic Resonance For The Estimation Of Cerebral Blood Flow And Oxygen Consumption", vol. 179, No. 2, 1991, pp. 954–961.
G. D. Mateescu et al, "Oxygen–17 Magnetic Resonance: In Vivo Detection Of Nascent Mitochondrial Water In Animals Breathing 17$_{02}$ Enriched Air", Case Western Reserve University, Cleveland, Ohio.
W. A. Edelstein et al., "Spin Warp NMR Imaging And Applications To Human Whole–Body Imaging", Letters to the Editor, pp. 751–756, 1980.
G. D. Mateescu et al., Combined 17 O/1 H magnetic resonance microscopy in plants, animals and materials: present status a potential, Case Western Reserve University, Cleveland, Ohio.
J. Pekar et al., In vivo measurement of cerebral oxygen consumption and blood flow using 17 O magnetic resonance imaging, Magnetic Resonance in Medicine, 21, 313–319 (1991).
S. Meiboom and D. Gill, Modified spin–echo method for measuring Sincerely, laxation times, The Review of Scientific Instrument vol. 29, No. 8, 1958.
Kwong, K. K., et al., Communications: Proton NMR Imaging of Cerebral Blood Flow Using H2–17O, Journal of Magnetic Resonance in Medicine, 22, 154–158, 1992.
Shaka, A. J., et al., Computer–Optimized Decoupling Scheme for Wideband Applications and Low–Level Operation, Journal of Magnetic Resonance, 64, 547–552, 1985.
A. L. Hopkins, et al., Oxygen–17 Compounds as Potential NMR T2 Contrast Agents: Enrichment Effects of H2 17O on Protein Solutions and Living Tissues, Mag. Res. in Med., 4, 399–403, 1987.
A. L. Hopkins, et al., Improved Sensitivity of Proton MR to Oxygen–17 as a Contrast Agent Using Fast Imaging: Detection in Brain, Mag. Res. in Med., 7, 222–229, 1988.

*Primary Examiner*—Krista M. Zele
*Attorney, Agent, or Firm*—Cushman, Darby & Cushman

[57] ABSTRACT

A method of measuring the $^{17}$O isotope content and distribution in a body by magnetic resonance imaging (MRI) by collecting first and second nuclear magnetic resonance (NMR) signals of the body under the same conditions of examination except that before one examination, the body is first irradiated with radio waves at the $^{17}$O resonance frequency, whereas before the other examination the body is not so irradiated. The difference in the results of the two examinations is measured to provide an NMR image of the $^{17}$O isotope distribution in the body.

9 Claims, 3 Drawing Sheets

METHOD OF MEASURING THE $^{17}O$ CONTENT AND DISTRIBUTION IN A BODY

FIELD AND BACKGROUND OF THE INVENTION

The present invention relates to a method of measuring the $^{17}O$ isotope content of a body, and particularly to such a method using nuclear magnetic resonance (NMR) spectroscopy examination techniques. Possible applications of the novel method of the invention include measuring the rate of perfusion of a solution administered to a living body, and measuring oxidative metabolism activity in a living body.

Oxygen appears in nature in the form of three stable (i.e, non-radioactive) isotopes, one with predominant abundance $^{16}O$ (99.76%), and two rare isotopes $^{17}O$ (0.037%) and $^{18}O$ isotope (0.20%). The isotopes $^{16}O$ and $^{18}O$ do not possess magnetic moment and therefore they do not have an effect on Nuclear Magnetic Resonance (NMR) spectroscopy, but the isotope $^{17}O$ does have a magnetic moment and therefore can be detected by NMR. The $^{17}O$ isotope also has an effect on other magnetic nuclei associated with it.

There are several applications where the detection of minute amounts of $^{17}O$ by NMR is important. One is the measurement of the rate of perfusion by Magnetic Resonance Imaging (MRI): J. Pekar et al., Magn. Reson. Med. 21, 313 (1991); K. K. Kwong et. al., Magn. Reson. Med. 22, 154 (1991). This is accomplished by injecting physiological solution containing $H_2^{17}O$ and following the rate of distribution of the $^{17}O$ isotope in the body. Another application is metabolic functional imaging: see J. Pekar et al., supra; also G. D. Mateescu et al., in "Synthesis and Applications of Isotopically Labelled Compounds"; T. A. Baillie and J. R. Jones Eds. Elsevier, Amsterdam, P.499 (1989). In this technique, molecular oxygen ($O_2$) labeled with the $^{17}O$ isotope is inhaled by the patient. Since $O_2$ is a paramagnetic molecule, it cannot be observed by NMR. However, in metabolic active respiring tissues, it is converted to $H_2O$ by oxygen metabolism.

There have been several suggestions in the literature (e.g., see above publications) of observing the $^{17}O$ isotope directly by NMR. However, because of the low sensitivity of $^{17}O$ NMR, and the high cost of $^{17}O$ enriched compounds, this approach seems impractical for medical applications.

The present invention is directed to a novel magnetic resonance imaging (MRI) method based on indirect detection of the $^{17}O$ isotope using $^1H$ (proton) NMR. Conventional magnetic resonance imaging (MRI) is exclusively based on the detection of the echo signal produced by protons after being stimulated by a sequence of strong radio frequency (RF) pulses generated at the resonance frequency of the protons in a magnetic field. Since most of the hydrogen in living tissues is present in water molecules, the image produced by MRI reflects the distribution of water in the observed object. Because of the high natural abundance (99.985%) of $^1H$ and its high gyromagnetic ratio, leading to high NMR sensitivity, proton MRI is by far the most commonly used MRI method.

OBJECTS AND BRIEF SUMMARY OF THE INVENTION

According to the present invention, there is provided a method of measuring the $^{17}O$ isotope content and distribution in a body by magnetic resonance imaging (MRI), comprising: collecting first and second NMR signals of the body under the same conditions of examination except that before one examination, the body had first been irradiated with radio waves at the $^{17}O$ resonance frequency, whereas before the other examination the body had not been so irradiated; and measuring the difference in the results of the two examinations to provide a nuclear magnetic resonance (NMR) image of the $^{17}O$ isotope distribution in the body.

According to further features in the preferred embodiment described below, the result of the difference between the two examinations is normalized by the sum of both examinations.

We have found that the increase in the transverse relaxation time ($T_2$) following the $^{17}O$ decoupling is directly related to the $^{17}O$ content of the sample. This finding explains the difference between the proton echo signal with irradiation of the $^{17}O$ resonance and without it, and enables the optimization of the echo time in order to maximize the difference between the echo signals, while preserving a high signal-to-noise ratio.

Possible applications of the novel method include measuring, by well known MRI techniques, the rate of perfusion of solutions containing water enriched with $^{17}O$ in the different parts of a living body, and measuring oxidative metabolism activity in a living body.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

The invention will be better understood by the following description of two examples of practicing the method in accordance with the present invention:

EXAMPLE 1

Figure 1:
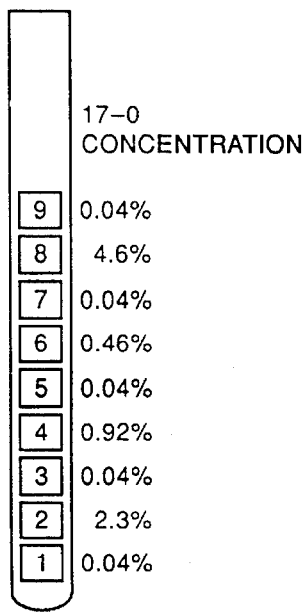
FIGS. 1 and 2 illustrate a setup used for measuring the $^{17}O$ isotope content of water in a series of glass bulbs in accordance with the method of the present invention.
Figure 2:
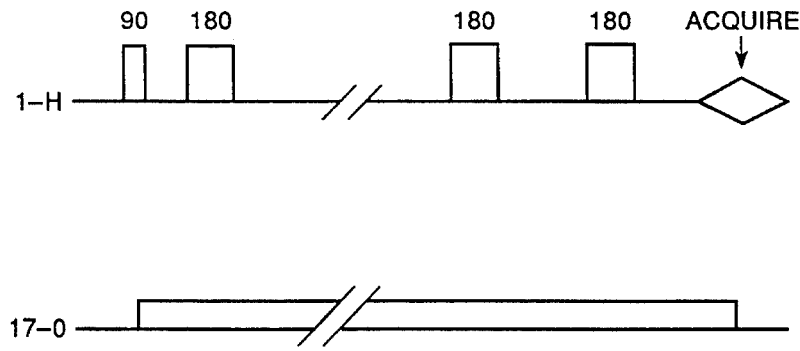

A one dimensional image of a sample was performed containing various concentrations of $^{17}O$ enriched water. The sample was a 5 mm NMR tube, filled with nine cylinders of about 4 mm height and 4 mm diameter. Each cylinder contained different amounts of $^{17}O$ enriched water, as shown in FIG. 1. The resonance frequency of the protons was 360 MHZ, and that of the $^{17}O$ was 48.6 MHz. The Z shim coil was used for the production of a gradient for one dimensional imaging (about 0.1 $G \cdot cm^{-1}$). The irradiation power at the $^{17}O$ frequency was about 30 watts, and may be applied either as continuous wave (CW) irradiation or according to a composite pulse coupling scheme, GARP: A. J. Shaka et al., J. Magn. Reson, 64, 547 (1985). The latter was used in the example shown. The pulse sequence of the experiment was a Carr-Purcell-Meiboom-Gill (CPMG) spin-echo sequence: H. Y. Carr and E. M. Purcell, Phys. Rev., 94, 630 (1954); S. Meiboom and D. Gill, Rev. Sci. Instrum., 29, 688 (1958) performed on the proton channel, in which the decoupling scheme on the $^{17}O$ channel took place between the first pulse (90°) and the beginning of the acquisition, as described in FIG. 2. The CPMG sequence was carried out with eight 180° pulses with a total echo time of 320 msec.

Figure 3:
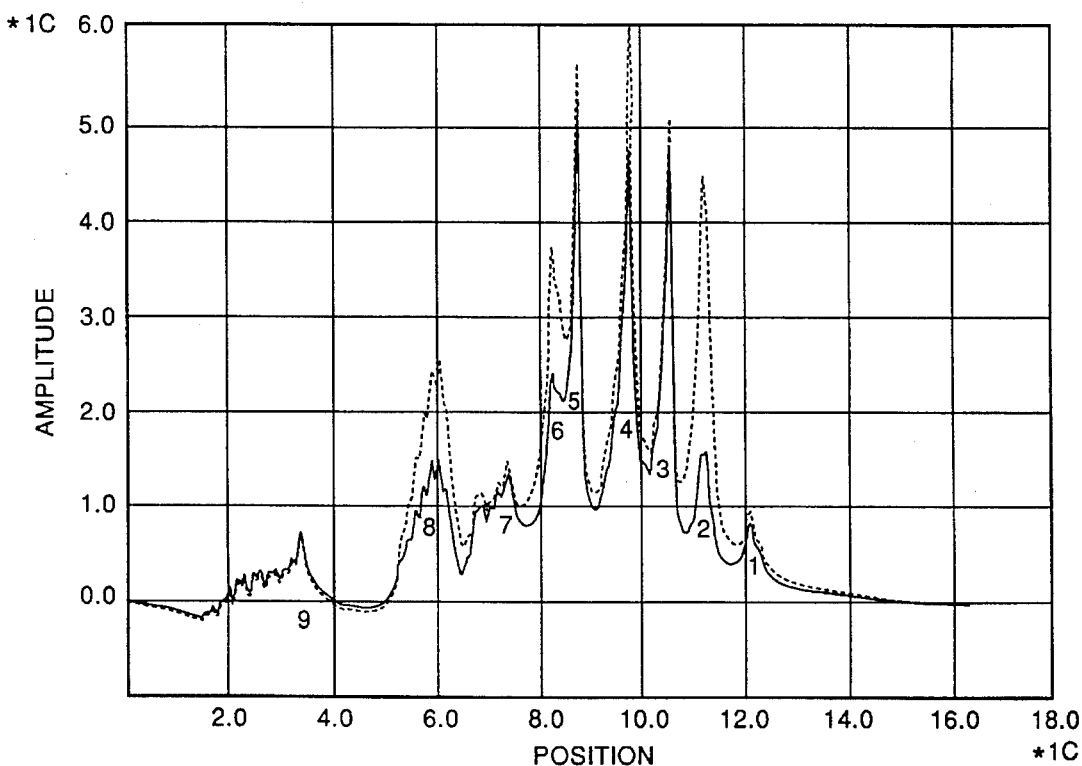
FIGS. 3 and 4 illustrate the results produced during one example of practicing the method according to the invention as described below.

FIG. 3 shows the two images. One image was obtained without irradiating at the $^{17}O$ resonance frequency (solid line), and the other image was obtained under the same conditions except with the irradiation (dotted line).

Figure 4:
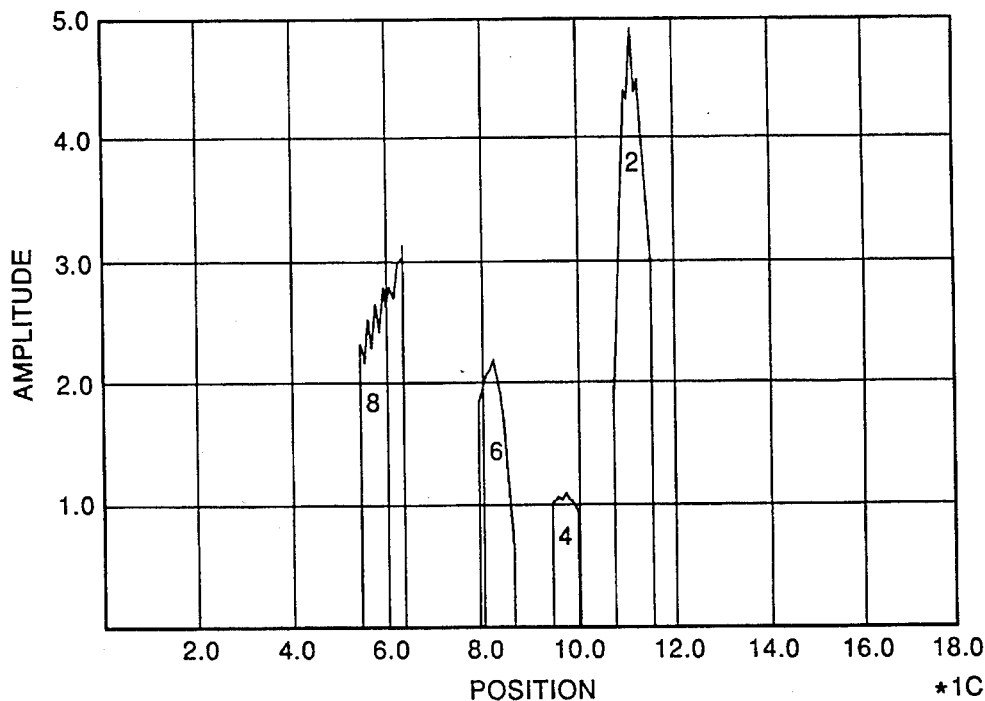

FIG. 4 shows the image obtained by subtraction of the image without irradiation of the $^{17}O$ from the one with irradiation. The resulting image was normalized by the sum of the two images in order to compensate for the non-linearity of the Z-gradient, and the different size of the proton signals resulting from r.f field inhomogeneity and uneven sensitivity along the sample. It is seen that the intensity of the image is roughly proportional to the $^{17}O$ content, except for the very high concentration of 4.6%, where the decoupling power was not enough to fully decouple the broadening due to the $^{17}O$ scalar coupling. However, in the practical implementation of the invention, only the low concentations of $^{17}O$ are of interest.

Similar results were obtained using an aqueous solution of 7% human serum albumin (HSA) instead of water. This solution had protein concentration similar to that of serum.

Figure 5:
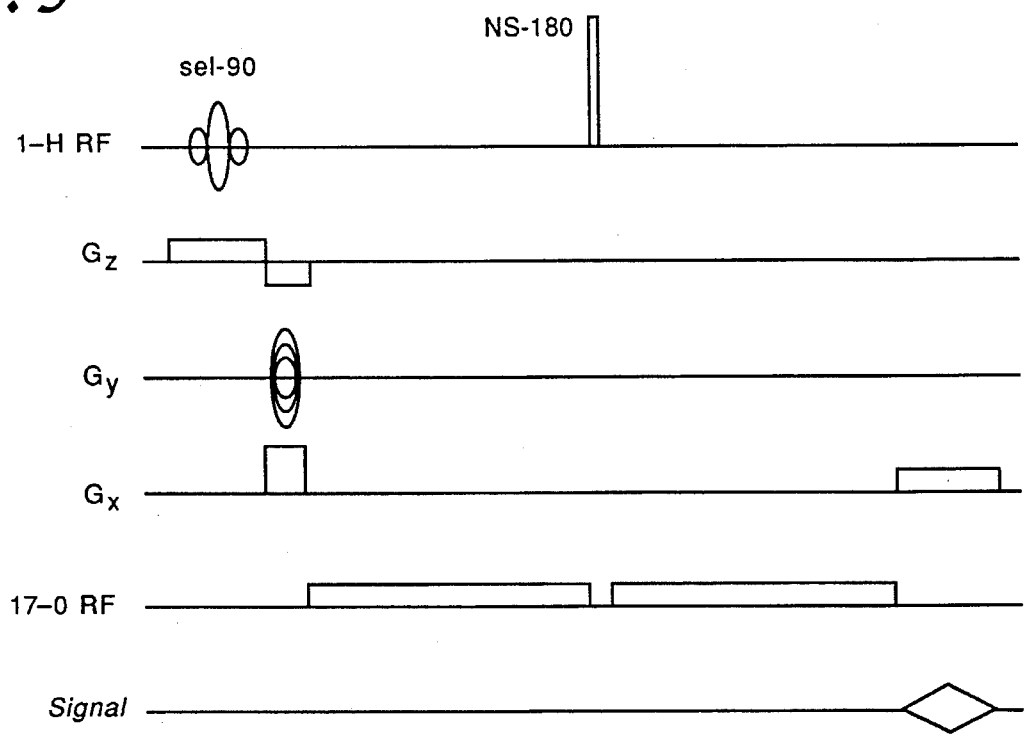
FIG. 5 illustrates one manner of applying the novel method for the NMR imaging of the body.

One way to apply the technique for NMR imaging (MRI) of the body is by using the modification of the spin-echo spin-warp technique as described in: W. A. Edelstein et al., Phys. Med. Biol., 25, 751 (1980), and as illustrated in FIG. 5. The above reference describes a pulse sequence to obtain an NMR signal representing the distribution of proton density in a body. FIG. 5 sets out a similar sequence but with the inclusion of an additional rf signal labelled 17-O RF. A first NMR signal is obtained by using the pulse sequence of FIG. 5, but without the inclusion of the signal 17-O RF. A second NMR signal is obtained by using the pulse sequence as shown in FIG. 5. The difference between the two NMR signals is taken to provide an NMR image of the $^{17}O$ isotope distribution in the body.

EXAMPLE 2

The second example is a demonstration of the potential application of the method as a tool for metabolic functional imaging. In this example, two live newborn mice were introduced into the NMR probe and were let to breath air mixed with 28% $^{17}O_2$, enriched oxygen. Consecutive direct $^{17}O$ measurements and indirect proton measurements using the method described above were taken on the same sample every 10-15 minutes. $^{17}O$ spectra were taken accumulating 128 scans. Proton spectra were taken using the CPMG spin echo sequence with TE=600 ms for the injection experiment and TE=1s for the respiration experiment. γ (CPMG) was 10 ms. Only one scan was collected for each proton spectrum: one with irradiation at the $^{17}O$ resonance frequency and one without it. Proton $T_2$ was 50 ms.

Figure 6:
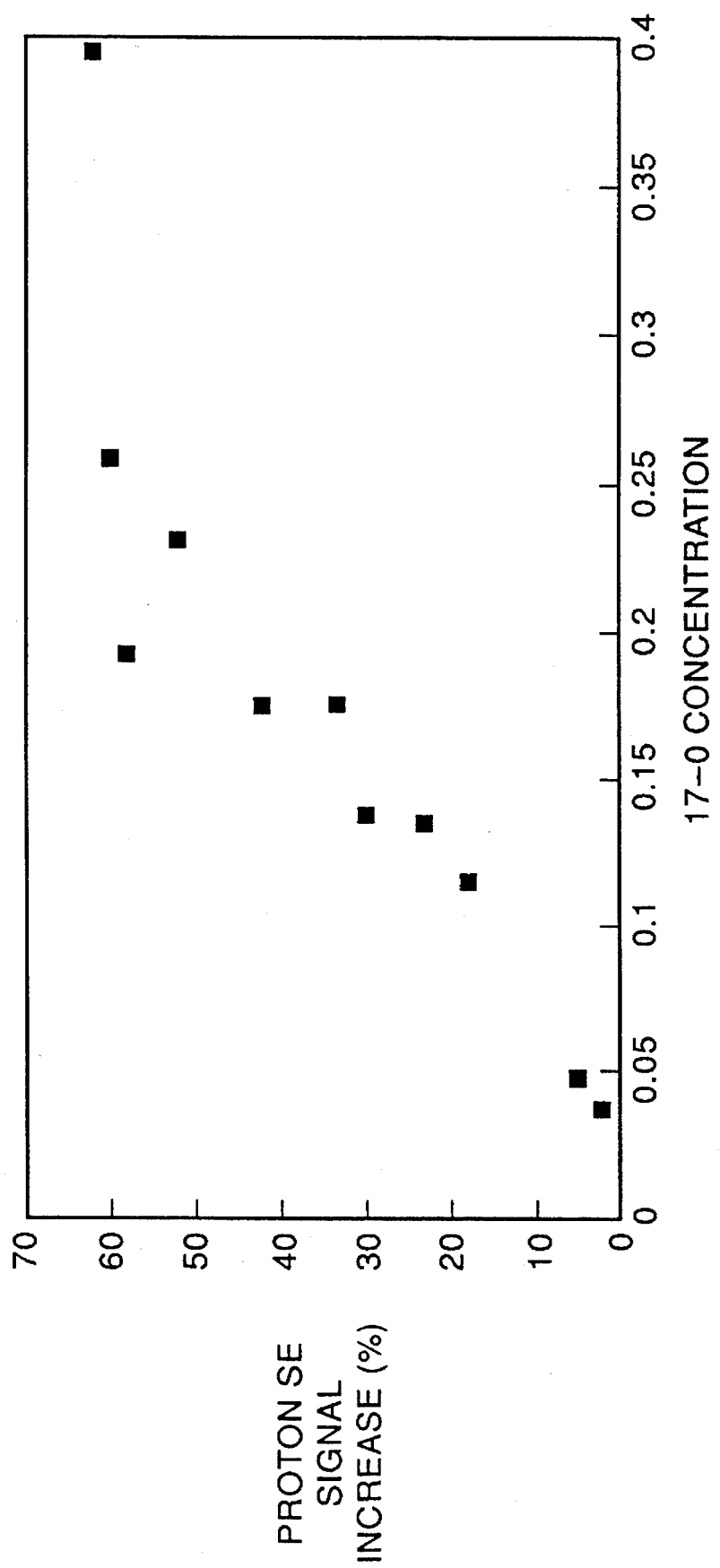
FIG. 6 illustrates the results produced during a second example of praticing the method according to the invention as described below.

FIG. 6 depicts the correlation between the direct $^{17}O$ measurements of $H_2^{17}O$ and the indirect measurements reflected by the increase in proton echo signal following an irradiation of the $^{17}O$ resonance. The graph shows that at low $H_2^{17}O$ concentrations, a fairly linear correlation exists between the $H_2^{17}O$ content as reflected by the direct $^{17}O$ measurements and the indirect measurements. The linearity is lost at about $H_2^{17}O$ concentration of 0.3%.

The invention thus provides a new method of indirect MRI of $^{17}O$, which is particularly useful for functional imaging of brain oxidative metabolic activity. This method is advantageous for several reasons: (a) it is highly sensitive even to minute amounts of $H_2^{17}O$ (down to 0.1%) and hence may reduce drastically the price of functional imaging experiments; (b) it reflects the amount of $H_2^{17}O$ in the tissue; (c) since $^{17}O$ resonance frequency in MRI instruments is relatively low, power deposition is relatively low; and (d) implementation of the pulse sequence to MRI is fairly straightforward, using interleaved sequences with and without $^{17}O$ decoupling, hence minimizing the error due to all time dependent effects.

While the invention is described with respect to two examples, it will be appreciated that many variations, modifications and other applications of the invention may be made.

We claim:

1. A method of measuring a content and a distribution of $^{17}O$ isotopes in a body, comprising steps of:
   applying a first magnetic resonance imaging sequence to the body when the body is not irradiated with radio waves at a $^{17}O$ resonance frequency;
   collecting a first nuclear magnetic resonance signal from the body;
   irradiating the body with radio waves at the $^{17}O$ resonance frequency;
   applying a second magnetic resonance imaging sequence to the body;
   collecting a second nuclear magnetic resonance signal from the body; and
   measuring a difference between the first nuclear magnetic resonance signal and the second nuclear magnetic resonance signal, the difference providing a nuclear magnetic resonance image of the distribution of the $^{17}O$ isotopes in the body.

2. The method according to claim 1, wherein the difference between the first nuclear magnetic resonance signal and the second nuclear magnetic resonance signal is normalized by a sum of the first nuclear magnetic resonance signal and the second nuclear magnetic resonance signal.

3. The method according to claim 1, wherein:
   the first nuclear magnetic resonance signal and the second nuclear magnetic resonance signal each comprise proton echo signals; and
   the difference in the respective proton echo signals of the first nuclear magnetic resonance signal and the second nuclear magnetic resonance signal is measured to provide a measurement of the $^{17}O$ isotope content of the body.

4. A method of measuring a rate of perfusion of a solution within a living body comprising steps of:
   administering to the living body a solution containing $H_2^{17}O$; and
   detecting a rate of distribution of $^{17}O$ isotopes in the living body, the step of detecting comprising steps of:
   applying a first magnetic resonance imaging sequence to the living body when the living body is not irradiated with radio waves at a $^{17}O$ resonance frequency;
   collecting a first nuclear magnetic resonance signal from the living body;
   irradiating the living body with radio waves at the $^{17}O$ resonance frequency;

applying a second magnetic resonance imaging sequence to the living body;

collecting a second nuclear magnetic resonance signal from the living body; and measuring a difference between the first nuclear magnetic resonance signal and the second nuclear magnetic resonance signal, the difference providing a nuclear magnetic resonance image of a distribution of the $^{17}O$ isotopes in the living body.

5. The method according to claim 4, wherein the difference between the first nuclear magnetic resonance signal and the second nuclear magnetic resonance signal is normalized by a sum of the first nuclear magnetic resonance signal and the second nuclear magnetic resonance signal.

6. The method according to claim 4, wherein:

the first nuclear magnetic resonance signal and the second nuclear magnetic resonance signal each comprise proton echo signals; and the difference in the respective proton echo signals of the first nuclear magnetic resonance signal and the second nuclear magnetic resonance signal is measured to provide a measurement of the $^{17}O$ isotope content of the living body.

7. A method of measuring oxidative metabolism activity in a living body, comprising steps of:

administering oxygen including $^{17}O$ isotopes to the living body; and detecting a content of the $^{17}O$ isotopes in the living body, the step of detecting comprising steps of:

applying a first magnetic resonance imaging sequence to the living body when the living body is not irradiated with radio waves at a $^{17}O$ resonance frequency;

collecting a first nuclear magnetic resonance signal from the living body;

irradiating the living body with radio waves at the $^{17}O$ resonance frequency;

applying a second magnetic resonance imaging sequence to the living body;

collecting a second nuclear magnetic resonance signal from the living body; and measuring a difference between the first nuclear magnetic resonance signal and the second nuclear magnetic resonance signal, the difference providing a nuclear magnetic resonance image of a distribution of the $^{17}O$ isotopes in the living body.

8. The method according to claim 7, wherein the difference between the first nuclear magnetic resonance signal and the second nuclear magnetic resonance signal is normalized by a sum of the first nuclear magnetic resonance signal and the second nuclear magnetic resonance signal.

9. The method according to claim 7, wherein:

the first nuclear magnetic resonance signal and the second nuclear magnetic resonance signal each comprise proton echo signals; and the difference in the respective proton echo signals of the first nuclear magnetic resonance signal and the second nuclear magnetic resonance signal is measured to provide a measurement of the $^{17}O$ isotope content of the living body.

* * * * *